US006337431B1

(12) United States Patent
Tricoli et al.

(10) Patent No.: US 6,337,431 B1
(45) Date of Patent: *Jan. 8, 2002

(54) TRANSGENIC PLANTS EXPRESSING DNA CONSTRUCTS CONTAINING A PLURALITY OF GENES TO IMPART VIRUS RESISTANCE

(75) Inventors: David M Tricoli; Kim J. Carney, both of Davis, CA (US); Paul F. Russell, Portage; Hector D. Quemada, Kalamazoo, both of MI (US); Russell J. McMaster, Kenosha, WI (US); John F. Reynolds, Davis; Rosaline Z. Deng, Oceanside, both of CA (US)

(73) Assignee: Seminis Vegetable Seeds, Inc., Saticov, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,379

(22) PCT Filed: Jun. 7, 1995

(86) PCT No.: PCT/US95/06261

§ 371 Date: Oct. 6, 1997

§ 102(e) Date: Oct. 6, 1997

(87) PCT Pub. No.: WO96/21031

PCT Pub. Date: Jul. 11, 1996

Related U.S. Application Data

(63) Continuation of application No. 08/366,991, filed on Dec. 30, 1994.

(51) Int. Cl.$^7$ .................. C12N 15/82; C12N 15/84; A01H 5/00; A01H 5/10
(52) U.S. Cl. .................. 800/280; 435/320.1; 435/419; 435/468; 435/469; 800/288; 800/301; 800/294; 800/317
(58) Field of Search ................. 800/205, 278, 800/279, 280, 288, 295, 298, 301, 317; 435/172.3, 320.1, 69.1, 410, 419, 468; 536/23.72

(56) References Cited

U.S. PATENT DOCUMENTS

| | | | |
|---|---|---|---|
| 4,970,168 A | 11/1990 | Turner | 435/317.1 |
| 5,217,902 A | 6/1993 | Jones et al. | 435/320.1 |
| 5,278,057 A | 1/1994 | Jorgensen | 435/172.3 |

FOREIGN PATENT DOCUMENTS

| | | | |
|---|---|---|---|
| EP | 578627 | | 7/1993 |
| WO | WO 9002185 | | 3/1990 |
| WO | WO 9110725 | | 7/1991 |
| WO | WO 94/28147 | * | 12/1994 |
| WO | WO 9428147 A | | 12/1994 |

OTHER PUBLICATIONS

Allison et al., *Virology*, 147, 309 (1985).
Allmansberger et al., *Molec. Gen. Genet.*, 198, 514 (1985).
An, *Methods in Enzymol.*, 153, 292 (1987).
An, *Plant Physiol.*, 81,86 (1986).
Bevan et al., *Nucleic Aicds Res.*, 11, 369 (1983).
Carrington et al., *J. Virol.*, 61, 2540 (1987).
Choi et al., *Plant Cell Reports*, 344 (1944).
Clark et al., *J. Gen Virol.*, 34, 475 (1979).
Clark et al., *J. Gen. Virol.*, 34, 475 (1977).
Crossway et al,, *Mol. Gen. Genet.*, 202, 179 (1985).
Depicker et al., *J. Mol. Appl. Genet.*, 1, 561–564 (1982).
Dougherty et al., *Virology*, 146, 282 (1985).
Fitch et al., *Bio/Technology*, 10, 1466 (1992).
Fromm et al., *Proc. Natl. Acad. Sci. USA*, 82, 824 (1985).
Glover, *DNA Cloning vol. II* (1985).
Herrera–Estrella, *Nature*, 303, 209 (1983).
Hoekema et al., *Bio/Technology*, 7, 273 (1989).
Hu et al., *Arch. Virol.*, 130, 17 (1993).
Jefferson et al., *EMBO J.*, 6, 3901 (1987).
Kay et al., *Nucl. Acids Res*, 15, 2778 (1987).
Lawson et al., *Biotechnology*, 8, 127 (1990).
Ling et al., *Bio/Technology*, 9, 752 (1991).
Loesch–Fries et al, *EMBO J.*, 6, 1845 (1987).
Miller, *Experiments in Molecular Genetics* (1972).
Namba et al. *Phytopathology*, 82, 940 (1992).
Namba et al., *Gene*, 107, 81 (1991).
Nelson et al., *Bio/Technology*, 6, 403 (1988).
Paszkowski et al., *EMBO J.*, 3, 2717 (1984).
Polites et al., *Biotechniques*, 4, 514–520 (1987).
Powell Abel et al., *Science*, 232, 738 (1986).
Provvidenti, *Plant Viruses of Horticultural Crops in the Tropics and Subtropics*, Taiwan, Rep. Of China (1986).
Quemada et al., *J. Gen. Virol*, 70, 1065 (1989).
Quemada et al., *J. Gen. Virol.*, 71, 1451 (1990).
Quemada et al., *Molec. Plant Pathol.*, 81, 794 (1991).
Sarmento et al., *Plant Cell tissue and Organ culture*, 31, 185 (1992).
Shukla et al., *Virology*, 152, 118 (1986).
Slightom, *Gene*, 100, 251 (1991).
Stark et al., *Biotechnology*, 7, 1257 (1989).

(List continued on next page.)

*Primary Examiner*—Elizabeth F. McElwain
*Assistant Examiner*—Ashwin Mehta
(74) *Attorney, Agent, or Firm*—Lisa V. Mueller; Gardner, Carton & Douglas

(57) ABSTRACT

The present invention provides a chimeric recombinant DNA molecule comprising: a plurality of DNA sequences, each of which comprises a plant-functional promoter linked to a coding region, which encodes a virus-associated coat protein, wherein said DNA sequences are preferably linked in tandem so that they are expressed in virus-susceptible plant cells transformed with said recombinant DNA molecule to impart resistance to said viruses; as well as methods for transforming plants with the chimeric recombinant DNA molecule and for selecting plants which express at least one of said DNA sequences imparting viral resistance.

16 Claims, 6 Drawing Sheets

OTHER PUBLICATIONS

Tricoli et al., *J. Cell. Biochem. Suppl.*, abstr. No. X1–126 (1994).

McMaster et al., *Phytopathology*, 83, 1425 (1993). Abstract No. A830.

Turner et al., *EMBO J.*, 6, 1181 (1987).

Van Dun et al., *Virology*, 164, 383 (1988).

Wu et al., *Methods in Enzymology*, 68 (1.

Chee, P.P. et al., J. Amer. Soc. Hort. Sct. 116(6):1098–1102(1991).

Nejidat, Ali et al., Physiologia Plantqrum 80: 662–668 Copenhagen 1990.

Wilson, T., Proc. Natl. Acad. Sci. USA vol. 90, pp. 3134–3141, Apr. 1993.

Matzke, M.A., et al., EMBO J., 8(3) 643–649 (1989).

Beck von Bodman, Susanne, et al., "Expression of Multiple Eukaryotic Genes from a Single Promoter in Nicotiana" *Biotechnology* 13:587–591, (1995).

Namba, Shigetou, et al., "Protection of Transgenic Plants Expressing the Coat Protein Gene of Watermelon Mosaic Virus II or Zucchini Yellow Mosaic Virus Against Six Potyviruses", *The American Phytopathological Society* 82(9):940–946, (1992).

Linn, F., et al., Epigenetic changes in the expression of the maize A1 gene in Petunia hybrida: Role of numbers of integrated gene copies and state of methylation, *Mol. Gen. Genet* 222:329–335, (1990).

Flavell, R.B., Inactivation of gene expression in plants as a consequence of specific sequence duplication, *Proc. Natl. Acad. Sci. USA*, 91:3490–3496, (1994).

Neuhuber, F., et al., Susceptibility of transgene loci to homology–dependent gene silencing, *Mol. Gen. Genet.* 244:230–241.

Quemada, Hector, D., et al., Expression of Coat Protein Gene from Cucumber Mosaic Virus Strain C in Tobacco: Protection Against Infections by CMV Strains Transmitted Mechanically or by Aphids, *Phytopathology*, 81:794–802, (1991).

Lawson et al. Engineering resistance to mixed virus infection in a commercial potato cultivar: resistance to potato virus X and potato virus Y in transgenic Russet Burbank. Bio/Techology. 8:127–134. Feb. 1990.*

Namba et al. Expression of the gene encoding the coat protein of cucumber mosaic virus (CMV) strain WL appears to provide protection to tobacco plants against infectio by several different CMV strains. Gene. 107:181–188, 1991.*

Namba et al. Protection of transgenic plants expressing the coat protein gene of watermelon mosaic virus II or zucchini yellow mosaic virus against six potyviruses. Phytopathology. 82(9):940–946, 1992.*

Choi et al. Genetic transformation and plant regeneration of watermelon using Agrobacterium tumefaciens. Plant Cell Reports. 13:344–348, 1994.*

* cited by examiner

TRANSGENIC PLANTS EXPRESSING DNA CONSTRUCTS CONTAINING A PLURALITY OF GENES TO IMPART VIRUS RESISTANCE

The present application is a 371 of PCT/US95/06261 filed on Jun. 7, 1995 which is a continuation of 08/366,991 filed on Dec. 30, 1994.

FIELD OF THE INVENTION

This invention is related to the genetic engineering of plants and to a means and method for conferring a plurality of traits, including resistance to viruses, to a plant using a vector encoding a plurality of genes, such as coat protein genes, protease genes, or replicase genes.

BACKGROUND OF THE INVENTION

Many agriculturally important crops are susceptible to infection by plant viruses, which can seriously damage a crop, reduce its economic value to the grower, and increase its cost to the consumer. Attempts to control or prevent infection of a crop by a plant virus have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Potyviruses are a distinct group of plant viruses which are pathogenic to various crops, and which demonstrate cross-infectivity between plant members of different families. Potyviruses include watermelon mosaic virus-2 (WMV-2); papaya ringspot virus strains papaya ringspot and watermelon mosaic I (PRV-p and PRV-w), two closely related members of the plant potyvirus group which were at one time classified as distinct virus types, but are presently classified as different strains of the same virus; zucchini yellow mosaic virus (ZYMV); potato virus Y; tobacco etch and many others. For example, see Table I of published European patent application 578,627.

These viruses consist of flexous, filamentous particles of dimensions approximately 780×12 nanometers. The viral particles contain a single-stranded RNA genome containing about 10,000 nucleotides of positive (+, coding, or sense) polarity. Translation of the RNA genome of potyviruses shows that the RNA encodes a single large polyprotein of about 330 kD. This polyprotein contains several proteins, one of which is a 49 kD protease that is specific for the cleavage of the polyprotein into at least six (6) other peptides. These proteins can be found in the infected plant cell and form the necessary components for viral replication. One of the proteins contained within this polyprotein is a 35 kD capsid or coat protein which coats and protects the viral RNA from degradation. Another protein is the nuclear inclusion protein, also referred to as replicase, which is believed to function in the replication of the viral RNA. In the course of a potyviral infection, the replicase protein (60 kDa, also referred to as the nuclear inclusion B protein) and the protease protein (50 kDa, also referred to as the nuclear inclusion I or nuclear inclusion A protein) are posttranslationally transported across the nuclear membrane into the nucleus of the plant cell at the later stages of viral infection and accumulate to high levels.

Generally, the coat protein gene is located at the 3'-end of the RNA, just prior to a stretch of terminal adenine nucleotide residues (200 to 300 bases). The location of the 49 Kd protease gene appears to be conserved in these viruses. In the tobacco etch virus, the protease cleavage site has been determined to be the dipeptide Gln-Ser, Gln-Gly or Gln-Ala. Conservation of these dipeptides as the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X, among others, in transgenic plants has resulted in plants which are resistant to infection by the respective virus. Some evidence of heterologous protection has also been reported. For example, Namba et al., *Phytopathology*, 82, 940 (1992) report that expression of coat protein genes from watermelon mosaic virus-2 or zucchini yellow mosaic virus in transgenic tobacco plants conferred protection against six other potyviruses: bean yellow mosaic virus, potato virus Y, pea mosaic virus, clover yellow vein virus, pepper mottle virus and tobacco etch virus. Stark et al., *Biotechnology*, 1, 1257 (1989) report that expression of the potyvirus soybean mosaic virus in transgenic plants provided protection against two serologically unrelated potyviruses: tobacco etch virus and potato virus Y.

However, expression of a preselected coat protein gene does not reliably confer heterologous protection to a plant. For example, transgenic squash plants containing the CMV-C coat protein gene and which have been shown to be resistant to CMV-C strain, are not protected against several highly virulent strains of CMV, including CMV-V-27 and CARNA-5. Thus, a need exists for improved methods to impart potyvirus resistance to plants.

SUMMARY OF THE INVENTION

The present invention provides a recombinant chimeric DNA molecule comprising a plurality of DNA sequences each of which comprises a promoter operably linked to a DNA sequence which encodes a virus-associated protein, such as a coat protein (cp), a protease, or a replicase, wherein said DNA sequences are expressed in virus-susceptible plant cells transformed with said recombinant DNA molecule to impart resistance to infection by each of said viruses. Preferably, the DNA sequences are linked in tandem, i.e., exist in head to tail orientation relative to one another. Also, preferably substantially equal levels of resistance to infection by each of said viruses occurs in plant cells transformed with said plurality of DNA sequences.

Preferably, each DNA sequence is also linked to a 3' non-translated DNA sequence which functions in plant cells to cause the termination of transcription and the addition of polyadenylated ribonucleotides to the 3' end of the transcribed mRNA sequences. Preferably, the virus is a plant-associated virus, such as a potyvirus.

Thus, the present DNA molecule can be employed as a chimeric recombinant "expression construct," or "expression cassette" to prepare transgenic plants that exhibit increased resistance to infection by at least two plant viruses, such as potyviruses. The present cassettes also preferably comprise at least one selectable marker gene or reporter gene which is stably integrated into the genome of the transformed plant cells in association with the viral genes. The selectable marker and/or reporter genes facilitate identification of transformed plant cells and plants. Preferably, the virus gene array is flanked by two or more selectable marker genes, reporter genes or a combination thereof. Another aspect of the present invention is a method of preparing a virus-resistant plant, such as a dicot, comprising:

(a) transforming plant cells with a chimeric recombinant DNA molecule comprising a plurality of DNA sequences, each comprising a promoter functional in said plant cells, operably linked to a DNA sequence, which encodes a protein associated with a virus which is capable of infecting said plant;

(b) regenerating said plant cells to provide a differentiated plant; and (c) identifying a transformed plant which expresses the DNA sequences so as to render the plant resistant to infection by said viruses, preferably at substantially equal levels of resistance to infection by each virus.

Yet another object of the present invention is to provide a method for providing resistance to infection by viruses in a susceptible Cucurbitaceae plant which comprises:

(a) transforming Cucurbitaceae plant cells with a DNA molecule encoding a plurality of proteins from viruses which are capable of infecting said Cucurbitaceae plant;

(b) regenerating said plant cells to provide a differentiated plant; and (c) selecting a transformed Cucurbitaceae which expresses the virus proteins at levels sufficient to render the plant resistant to infection by said viruses.

It is a further object of the present invention to provide multi-virus resistant transformed plant which contains stably-integrated DNA sequences encoding virus proteins.

It is still a further object of the present invention to provide virus resistant transformed plant cells which contain a plurality of viral genes, i.e., 2–7 or more genes, which are expressed as virus proteins from the same virus strain, from different virus strains as from different members of the virus group, such as the potyvirus group.

The present invention is exemplified primarily by the insertion of multiple virus cp expression cassettes into a binary plasmid and subsequent characterization of resulting plasmids. Combinations of CMV, ZYMV, WMV-2, SQMV, and PRV coat protein expression cassettes were placed in the binary plasmid pPRBN. Subsequently, binary plasmids harboring multiple cp expression cassettes were mobilized into Agrobacterium for use in plant transformation procedures. Binary plasmids harboring multiple expression cassettes are employed to transfer two or more virus coat protein transformation-susceptible genes into plants, such as members of the Cucurbitaceae family, along with the associated selectable marker and/or reporter genes.

Thus, the present invention provides a genetic engineering methodology by which multiple traits can be manipulated and tracked as a single gene insert, i.e., as a construct which acts as a single gene which segregates as a single Mendelian locus. Although the invention is exemplified via virus resistance genes, in practice, any combination of genes could be linked. Therefore one could track a block of genes that provide traits such as disease resistance, plus enhanced herbicide resistance, plus extended shelf life, and the like, by simply tracking the linked selectable marker or reporter gene which has been incorporated into the transformation vector.

It was also discovered that when multiple tandem genes are inserted, they preferably all exhibit substantially the same degrees of efficacy, and more preferably substantially equal degrees of efficacy, wherein the term "substantial" as it relates to viral resistance is defined with reference to the assays described in the examples hereinbelow. For example, if one examines numerous transgenic lines containing an intact ZYMV and WMV-2 coat protein insert, one finds that if a line is immune to infection by ZYMV it is also immune to infection by WMV-2. Similarly, if a line exhibits a delay in symptom development to ZYMV it will also exhibit a delay in symptom development to WMV2. Finally, if a line is susceptible to ZYMV it will be susceptible to WMV-2. This phenomenon is unexpected. If there were not a correlation between the efficacy of each gene in these multiple gene constructs this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved).

If the efficacy of individual genes in a Ti plasmid containing multiple genes were independent, the probability of finding a transgenic line that was resistant to each targeted virus would decrease dramatically. For example, in a species in which there is a 10% probability of identifying a line with resistance using a single gene insert, is transformed with a triple-gene construct CZW and each gene display an independent levels of efficacy, the probability of finding a line with resistance to CMV, ZYMV and WMV-2 would be 0.1×0.1×0.1=0.001 or 0.1%. However, since the efficacy of multivalent genes is not independent of each other the probability of finding a line with resistance to CMV, ZYMV and WMV-2 is still 10% rather than 0.1%. Obviously this advantage becomes more pronounced as constructs containing four or more genes are used.

DETAILED DESCRIPTION OF THE INVENTION

Figure 1:
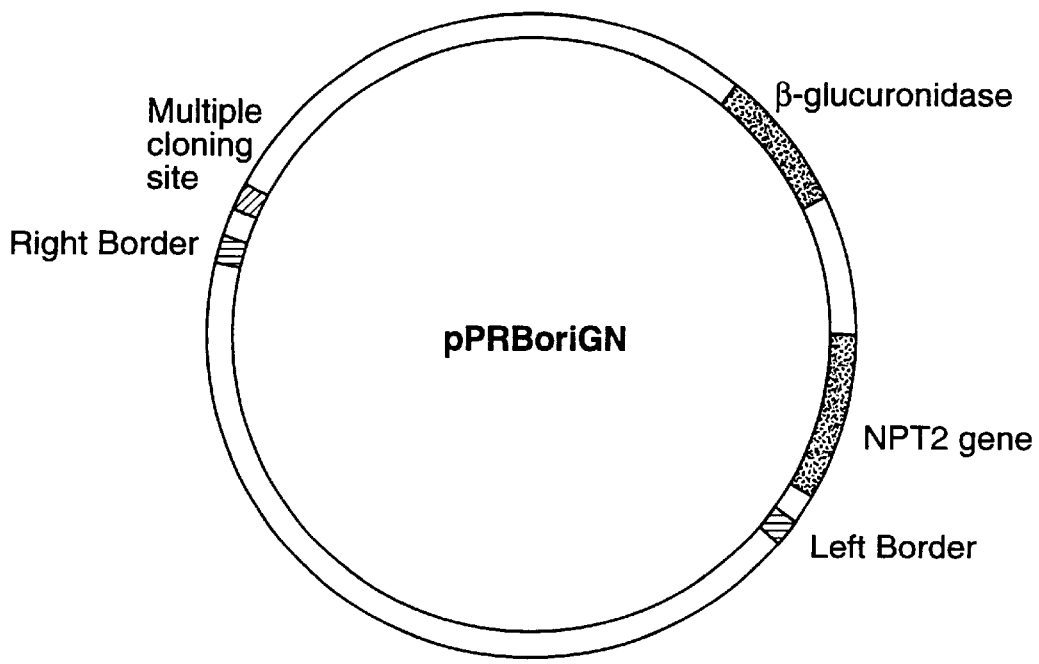
FIG. 1 depicts the structure of binary vector pPRBoriGN.

The vial resistance conferred to plants of the present invention is provided by the expression in planta of an isolated DNA sequence comprising nucleotides encoding a plurality, i.e., 2–7 virus proteins, such as coat proteins, proteases and/or replicases.

Representative viruses from which these DNA sequences can be isolated include, but are not limited to, potato virus X (PVX), potyviruses such as potato virus Y (PVY), cucomovirus (CMV), tobacco vein mottling virus, watermelon mosaic virus (WMV), zucchini yellow mosaic virus (ZYMV), bean common mosaic virus, bean yellow mosaic virus, soybean mosaic virus, peanut mottle virus, beet mosaic virus, wheat streak mosaic virus, maize dwarf mosaic virus, sorghum mosaic virus, sugarcane mosaic virus, johnsongrass mosaic virus, plum pox virus, tobacco etch virus, sweet potato feathery mottle virus, yam mosaic virus, and papaya ringspot virus (PRV), cucomoviruses, including CMA and comovirus.

Generally, a potyvirus is a single-stranded RNA virus that is surrounded by a repeating proteinaceous monomer, which is termed the coat protein (CP). The encapsidated virus has a flexous rod morphology. The majority of the potyviruses are transmitted in a nonpersistent manner by aphids. As can be seen from the wide range of crops affected by potyviruses, the host range includes such diverse families of plants, but is not limited to Solanaceae, Chenopodiaceae, Gramineae, Compositae, Leguminosae, Dioscrocaceae, Cucurbitaceae, and Caricaceae.

As used herein, with respect to a DNA sequence or "gene", the term "isolated" is defined to mean that the sequence is either extracted from its context in the viral genome by chemical means and purified and/or modified to the extent that it can be introduced into the present vectors in the appropriate orientation, i.e., sense or antisense. As used herein, the term "chimeric" is defined to mean the linkage of two or more DNA sequences which are derived from different sources, strains or species, i.e., from bacteria and plants, or that two or more DNA sequences from the same species are linked in a way that does not occur in the native genome. Thus, the DNA sequences useful in the present invention may be naturally-occurring, semi-synthetic or entirely synthetic. The DNA sequence may be linear or circular, i.e, may be located on an intact or linearized plasmid, such as the binary plasmids described below. As used herein, the term "heterologous" is defined to mean not identical, e.g. different in nucleotide and/or amino acid sequence, phenotype or an independent isolate. As used herein, the term "expression" means transcription or transcription followed by translation of a particular DNA molecule.

Most of the recombinant DNA methods employed in practicing the present invention are standard procedures, well known to those skilled in the art, and described in detail in, or example, European Patent Application Publication Number 223,452, published Nov. 29, 1986, which is incorporated herein by reference. Enzymes are obtained from commercial sources and are used according to the vendor's recommendations or other variations known in the art. General references containing such standard techniques include the following: R. Wu, ed. (1979) *Methods in Enzymology,* Vol. 68; J. H. Miller (1972) *Experiments in Molecular Genetics;* J. Sambrook et al. (1989) *Molecular Cloning: A Laboratory Manual* 2nd Ed.; D. M. Glover, ed. (1985) *DNA Cloning Vol. II;* H. G. Polites and K. R. Marotti (1987) "A step-wise protocol for cDNA synthesis," *Biotechniques* 4; 514–520; S. B. Gelvin and R. A. Schilperoort, eds. Introduction, Expression, and Analysis of Gene Products in Plants, all of which are incorporated by reference.

To practice the present invention, a viral gene must be isolated from the viral genome and inserted into a vector containing the genetic regulatory sequences necessary to express the inserted gene. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different courses exist to isolate a viral gene. To do so, one having ordinary skill in the art can use information about the genomic organization of potyviruses, cucumoviruses or comoviruses to locate and isolate the coat protein gene or the nuclear inclusion body genes. The coat protein gene in potyviruses is located at the 3' end of the RNA, just prior to a stretch of about 200–300 adenine nucleotide residues. The nuclear inclusion body B (NIb) gene is located just 5' to the coat protein gene, and the nuclear inclusion body A (NIa) gene is 5' to the NIb gene. Additionally, the information related to proteolytic cleavage sites is used to determine the N-terminus of the potyvirus coat protein gene and the N- and C-terminus of non-coat protein genes. The protease recognition sites are conserved in the potyviruses and have been determined to be either the dipeptide Gln-Ser, Gln-Gly or Gln-Ala. The nucleotide sequences which encode these dipeptides can be determined.

Using methods well known in the art, a quantity of virus is grown and harvested. The viral RNA is then separated and the viral gene isolated using a number of known procedures. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for the viral gene. These primers can include in addition to viral specific sequences, novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* to create a cDNA library.

Since potyvirus genes are generally conserved, oligonucleotides based on an analogous gene from a previous isolate or an analogous gene fragment from a previous isolate can be used as a hybridization probe to screen the cDNA library to determine if any of the transformed bacteria contain DNA fragments with the appropriate viral sequences. The cDNA inserts in any bacterial colonies which hybridize to these probes can be sequenced. The viral gene is present in its entirety in colonies which have sequences that extend 5' to sequences which encode a N-terminal proteolytic cleavage site and 3' to sequences which encode a C-terminal proteolytic cleavage site for the gene of interest.

Alternatively, cDNA fragments may be inserted in the sense orientation into expression vectors. Antibodies against a viral protein may be used to screen the cDNA expression library and the gene can be isolated from colonies which express the protein.

The nucleotide sequences encoding the coat protein genes and nuclear inclusion genes of a number of viruses have been determined and the genes have been inserted into expression vectors. The expression vectors contain the necessary genetic regulatory sequences for expression of an inserted gene. The coat protein gene is inserted such that those regulatory sequences are functional and the genes can be expressed when incorporated into a plant genome. Selected literature references to methods of isolating, cloning and expressing viral genes are listed on Table I, below.

TABLE I

Cloned Genes From RNA Viruses

| Viral Gene | Reference |
|---|---|
| Papaya ringspot cp | M. M. Fitch et al., Bio/Technology, 10, 1466 (1992) |
| Potato virus X cp | K. Ling et al., Bio/Technology, 9, 752 (1991); A. Hoekema et al., Bio/Technology, 7, 273 (1989) |
| Watermelon Mosaic Virus II cp | H. Quemada et al., J. Gen. Virol., 71, 1451 (1990); S. Namba et al., Phytopathology, 82, 940 (1992) |
| Zucchini yellow Mosaic Virus cp | S. Namba et al., Phytopathology, 82, 940 (1992) |
| Tobacco Mosaic Virus cp | R. S. Nelson et al., Bio/Technology, 6, 403 (1988); P. Powell Abel et al., Science, 232, 738 (1986) |
| Alfalfa Mosaic Virus cp | Loesch-Fries et al., EMBO J., 6, 1845 (1987); N. E. Turner et al., EMBO J., 6, 1181 (1987) |
| Soybean Mosaic Virus cp | D. M. Stark et al., Biotechnology, 7, 1257 (1989) |
| Cucumber Mosaic Virus strain C cp | H. Q. Quemada et al., Molec. Plant Pathol., 81, 794 (1991) |
| Cucumber Mosaic Virus strain WL cp | UpJohn Co. (PCT WO90/02185) |
| Tobacco etch virus cp | Allison et al., Virology, 147, 309 (1985) |
| Tobacco etch virus nuclear inclusion protein | J. C. Carrington et al., J. Virol., 61, 2540 (1987) |
| Pepper Mottle Virus cp | W. G. Dougherty et al., Virology 146, 282 (1985) |
| Potato virus Y cp | D. D. Shukla et al., Virology, 152, 118 (1986) |
| Potato virus Y nuclear inclusion protein | European Patent Application 578,627 |
| Potato virus X cp | C. Lawson et al., Biotechnology, 8, 127 (1990) |
| Tobacco streak virus (TSV) cp | C. M. Van Dun et al., Virology, 164, 383 (1988) |

In order to express the viral gene, the necessary genetic regulatory sequences must be provided. Since the proteins encoded in a potyvirus genome are produced by the post translational processing of a polyprotein, a viral gene isolated from viral RNA does not contain transcription and translation signals necessary for its expression once transferred and integrated into a plant genome. It must, therefore, be engineered to contain a plant expressible promoter, a translation initiation codon (ATG) and a plant functional poly(A) addition signal (AATAAA) 3' of its translation termination codon. In the present invention, a viral gene is inserted into a vector which contains cloning sites for insertion 3' of the initiation codon and 5' of the poly(A) signal. The promoter is 5' of the initiation codon such that when structural genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present viral gene expression cassettes include the constitutive promoters from CaMV, the Ti genes nopaline synthase (Bevan et al., *Nucleic Acids Res. II*, 369–385 (1983)) and octopine synthase (Depicker et al., *J. Mol. Appl. Genet.*, 1, 561–564 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or the RNAs effective to provide viral resistance, but not so much as to be detrimental to the cell in which they are expressed. The promoters selected should be capable of functioning in tissues including but not limited to epidermal, vascular, and mesophyll tissues. The actual choice of the promoter is not critical, as long as it has sufficient transcriptional activity to accomplish the expression of the preselected proteins or antisense RNA, and subsequent conferral of viral resistance to the plants.

The non-translated leader sequence can be derived from any suitable source and can be specifically modified to increase the translation of the mRNA. The 5' non-translated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

The termination region or 3' non-translated region which is employed is one which will cause the termination of transcription and the addition of polyadenylated ribonucleotides to the 3' end of the transcribed mRNA sequence. The termination region may be native with the promoter region, native with the structural gene, or may be derived from another source, and preferably include a terminator and a sequence coding for polyadenylation. Suitable 3' non-translated regions of the chimeric plant gene include but are not limited to: (1) the 3' transcribed, non-translated regions containing the polyadenylation signal of Agrobacterium tumor-inducing (Ti) plasmid genes, such as the nopaline synthase (NOS) gene, and (2) plant genes like the soybean 7S storage protein genes.

Selectable marker genes may be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like. For example, see Table 1 of PCT WO/91/10725, cited above. The present invention also envisions replacing all of the virus-associated genes with an array of selectable marker genes.

The particular marker employed will be one which will allow for the selection of transformed cells as opposed to those cells which were not transformed. Depending on the number of different host species one or more markers may be employed, where different conditions of selection would be useful to select the different host, and would be known to those of skill in the art. A screenable marker or "reporter gene" such as the β-glucuronidase gene or luciferase gene may be used in place of, or with, a selectable marker. Cells transformed with this gene may be identified by the production of a blue product on treatment with 5-bromo-4-chloro-3-indoyl-β-D-glucuronide (X-Gluc).

In developing the present expression construct, the various components of the expression construct such as the DNA sequences, linkers, or fragments thereof will normally be inserted into a convenient cloning vector, such as a plasmid or phage, which is capable of replication in a bacterial host, such as E. coli. Numerous cloning vectors exist that have been described in the literature. After each cloning, the cloning vector may be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in E. coli cells.

All DNA manipulations are typically carried out in E. coli cells, and the final plasmid bearing the potyvirus expression cassette is moved into Agrobacterium cells by direct DNA transformation, conjugation, and the like. These Agrobacterium cells will contain a second plasmid, also derived from Ti or Ri plasmids. This second plasmid will carry all the vir genes required for transfer of the foreign DNA into plant cells.

Suitable plant transformation cloning vectors include those derived from a Ti plasmid of *Agrobacterium tumefaciens*, as generally disclosed in Glassman et al. (U.S. Pat. No. 5,258,300). In addition to those disclosed, for example, Herrera-Estrella, *Nature*, 303, 209 (1983), Biotechnica (published PCT application PCT WO/91/10725), and U.S. Pat. No. 4,940,838, issued to Schilperoort et al.

A variety of techniques are available for the introduction of the genetic material into or transformation of the plant cell host. However, the particular manner of introduction of the plant vector into the host is not critical to the practice of the present invention, and any method which provides for efficient transformation may be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, transformation using viruses or pollen, chemicals that increase the direct uptake of DNA (Paszkowski et al., *EMBO J.*, 3, 2717 (1984)), microinjection (Crossway et al., *Mol. Gen. Genet.*, 202, 179 (1985)), electroporation (Fromm et al., *Proc. Natl. Acad. Sci. USA*, 82, 824 (1985)), or high-velocity microprojectiles (Klein et al., *Nature*, 327, 70 (1987)).

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present multi-gene expression cassette for an effective period of time. This may range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove non-resistant sections. The cells or calli can then be assayed for the presence of the viral gene cassette, or may be subjected to known plant regeneration protocols. In protocols involving the direct production of shoots, those shoots appearing on the selective media are presumed to be transformed and may be excised and rooted, either on selective medium suitable for the production of roots, or by simply dipping the excised shoot in a root-inducing compound and directly planting it in vermiculite.

In order to produce transgenic plants exhibiting multi-viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity to that of the viral genomic RNA such that they are capable of base pairing with viral specific RNA of the opposite polarity to that of viral genomic RNA under conditions described in Chapter 7 of Sambrook et al. (1989). mRNA molecules also encompassed within the scope of the invention are those which contain viral specific sequences derived from the viral genes present in the transformed vector which are of the opposite polarity to that of the viral genomic RNA such that they are capable of base pairing with viral genomic RNA under conditions described in Chapter 7 of Sambrook et al. (1989).

The presence of a viral gene can also be detected by immunological assays, such as the double-antibody sandwich assays described by Namba et al., *Gene,* 107, 181 (1991) as modified by Clark et al., *J. Gen. Virol.,* 34, 475 (1979). See also, Namba et al., *Phytopathology,* 82, 940 (1992).

Virus resistance can be assayed via infectivity studies as generally disclosed by Namba et al., ibid., wherein plants are scored as symptomatic when any inoculated leaf shows veinclearing, mosaic or necrotic symptoms.

It is understood that the invention is operable when either sense or anti-sense viral specific RNA is transcribed from the expression cassettes described above. That is, there is no specific molecular mechanism attributed to the desired phenotype and/or genotype exhibited by the transgenic plants. Thus, protection against viral challenge can occur by any one or any number of mechanisms.

It is also understood that virus resistance can occur by the expression of any virally encoded gene. Thus, transgenic plants expressing a coat protein gene or a non-coat protein gene can be resistant to challenge with a homologous or heterologous virus. For example, a transgenic plant harboring a PRV NIa protease gene was found to be resistant to challenge with PRV (see Table 7, Example III), a transgenic plant harboring a WMV-2 FL strain of coat protein gene was resistant to challenge with a heterologous strain of virus, WMV-2 NY (Tables 1–8, Examples I–IV), and a transgenic plant harboring a CMV-C coat protein gene was somewhat resisitant to challenge with ZYMV (for further information see Applicants' Assignees copending patent application Ser. No. 08/367,016 entitled "Transgenic Plants Exhibiting Heterologous Viral Protection" filed on Dec. 30, 1994, now abandoned, incorporated by reference herein).

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. The farmer typically grows more than one kind of hybrid based on such differences as maturity, disease and insect resistance, color or other agronomic traits. Additionally, hybrids adapted to one part of a country are not adapted to another part because of differences in such traits as maturity, disease and insect tolerance, or public demand for specific varieties in given geographic locations. Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. With respect to transgenic plants of the type disclosed herein, the transgenes exhibit dominant, single gene Mendelian behavior. This genetic analysis can be part of the initial efforts to covert agronomically elite, yet sensitive lines to resistant lines. A conversion process (backcrossing) is carried out by crossing the original resistant line with a sensitive elite line and crossing the progeny back to the sensitive parent. The progeny from this cross will segregate such that some plants carry the resistance gene(s) whereas some do not. Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate backcrossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

The invention will be further described by reference to the following detailed examples.

EXAMPLE I

Squash Varieties with Multiple Virus Resistance

A. Binary Plasmid Vectors

The DNA which was transferred into the plant genomes was contained in binary plasmids (M. Bevan, *Nucleic Acids Res.,* 11, 369 (1983)). The parent binary plasmid was PGA482, constructed by G. An, *Plant Physiol.,* 81, 86 (1986). This vector contains the T-DNA border sequences from pTiT37, the selectable marker gene Nos-NPT II (which contains the plant-expressible nopaline gene promoter fused to the bacterial NPT II gene obtained from Tn5), a multiple cloning region, and the cohesive ends of phage lambda.

The plasmid pPRBoriGN (FIG. 1) was derived from the plasmid PGA482 as follows: A bacterial selectable marker, gentamycin resistance, (R. Allmansberger, et al., *Molec. Gen. Genet.,* 198, 514 (1985)) was inserted adjacent to the right border ($B_R$), but outside the T-DNA region. The Nos-NPT II gene was then excised and the multiple cloning site (MCS) was regenerated adjacent to $B_R$, just inside the T-DNA region. Next, a plant-expressible β-glucuronidase (GUS) gene cassette (R. A. Jefferson, et al., *EMBO J.*, 6, 3901(1987)) was inserted within the T-DNA region adjacent to the pBR322 origin of replication. Finally, a plant-expressible NPT II gene was inserted inside the T-DNA region adjacent to the left border ($B_L$). This NPT II gene was produced by insertion of the NPT II coding region into the expression cassette of the *E. coli* plasmid pDH51 (R. Kay et al., *Nucl. Acids Res.*, 15, 2778 (1987)). This provided a cauliflower mosaic virus (CaMV) 35S promoter polyadenylation signal.

Figure 2:
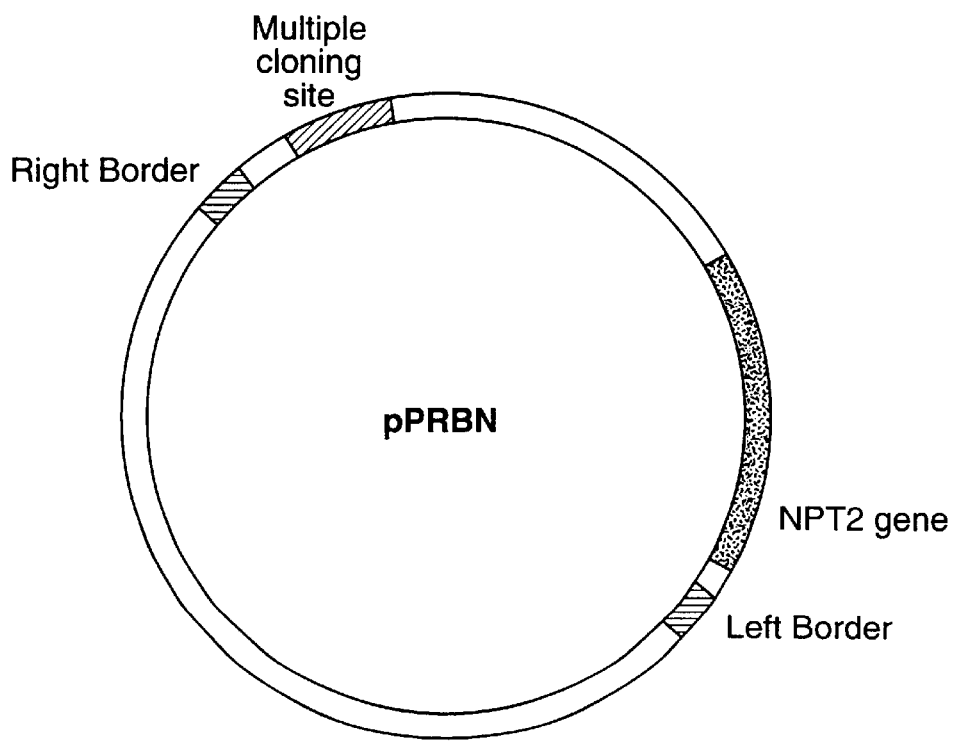
FIG. 2 depicts the structure of binary vector pPRBN.

The plasmid pPRBN (FIG. 2) was derived from pPR-BoriGN as follows: The region of pPRBoriGN from the beginning of the GUS coding sequence to $B_L$ was deleted. Therefore, the GUS gene and 35S/NPT II cassette were removed as a unit. This region was then replaced by a fragment consisting of the 35S/NPT II cassette only. The net result of these steps was the removal of the GUS gene and a short region of pBR322 homology, leaving the plant expressible NPT II gene adjacent to $B_L$.

B. Donor Genes

1. Watermelon Mosaic Virus 2

Figure 3:
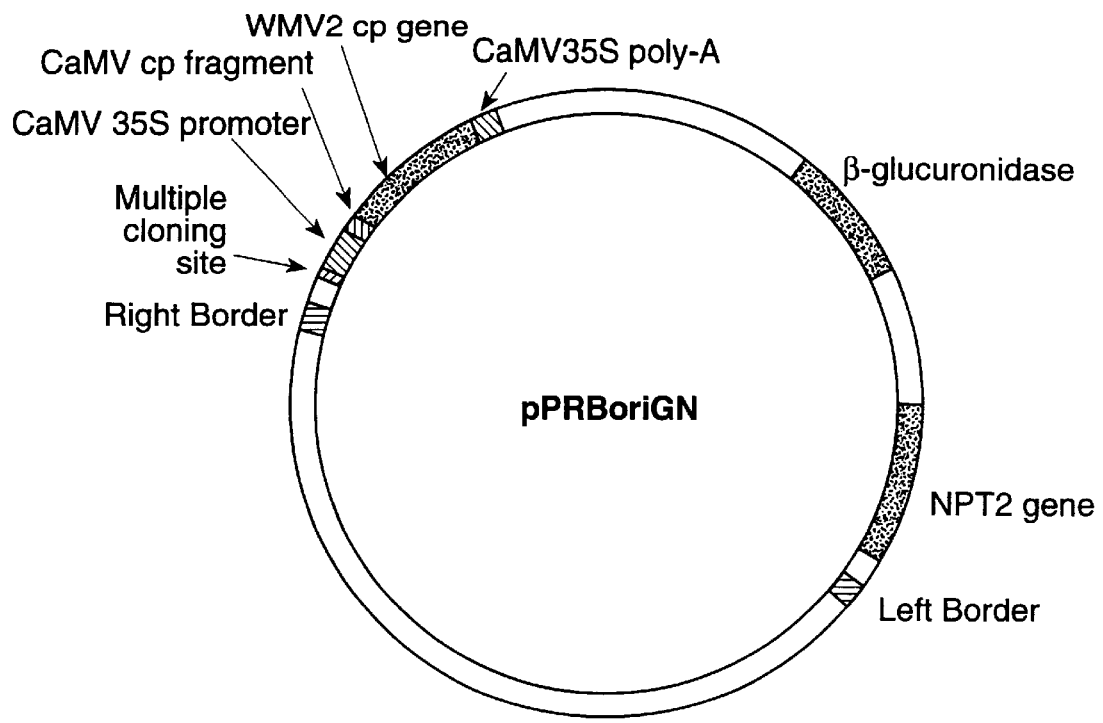
FIG. 3 depicts the structure of pPRCPW.

A plant-expressible WMV2 gene was constructed by using specific oligonucleotide primers to generate a fragment consisting of the WMV2 coat protein coding region from strain WMV-2 FL and flanking AatII (5') and BglII (3') restriction enzyme sites. This fragment was ligated to AatII/BglII-digested pUC19B$_2$, which is the plasmid pUC19 modified to contain the BglII restriction enzyme site in its multiple cloning region. The resulting plasmid, designated pUCWM2P$_{25}$, was further modified by the addition of the CaMV 35S promoter and polyadenylation signal obtained from pUC1813/CP19, (J. L. Slightom, *Gene*, 100, 251 (1991)) in order to produce a plant-expressible coat protein cassette. The protein produced by the expression of this gene should be a fusion between the WMV2 coat protein and the NH$_3$-terminal portion of the CMV coat protein gene. This cassette (CPW) was then excised by BamHI digestion and ligated to the BglII site of pPRBoriGN to produce the binary plasmid designated pPRCPW (FIG. 3).

2. Zucchini Yellow Mosaic Virus

The cloning and characterization of the ZYMV coat protein gene from strain ZYMV FL used herein is described in H. Quemada, et al., *J. Gen. Virol.*, 71, 1451 (1990). The strategy employed in the construction of a plant-expressible ZYMV coat protein gene is described by J. L. Slightom, (1991) cited above, and S. Namba et al., *Phytopathology*, 82, 945 (1992).

3. Cucumber Mosaic Virus

The cloning, characterization and engineering of the CMV coat protein gene used in our experiments are described in H. Quemada et al., *J. Gen. Virol.*, 70, 1065 (1989) and in the 1991 paper cited above.

4. Squash Mosaic Virus

SQMV is a comovirus that is transmitted by seed and spread by the striped or spotted cucumber beetles (Acalymma spp. and Diabrotica spp.). The insect acquires the virus within five minutes and the virus is retained for up to 20 days. The host range is limited to Cucurbitaceae. This virus consists of isometric particle 30 nm in diameter which contain single stranded RNA divided into two functional pieces called M-RNA and B-RNA (Provvidenti, in *Plant Viruses of Horticultural Crops in the Tropics and Subtropics*, Taiwan, Rep. of China (1986) at pages 20–36).

Figure 4:
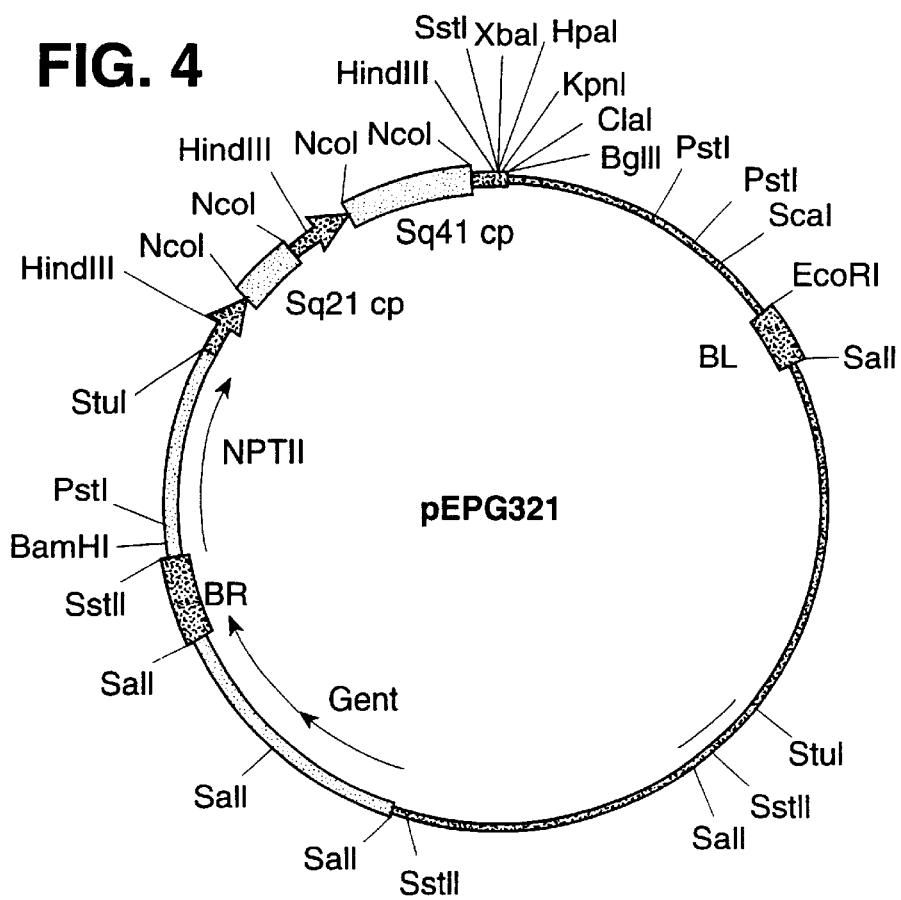
FIG. 4 depicts the structure of binary plasmid pEPG321.
Figure 11:
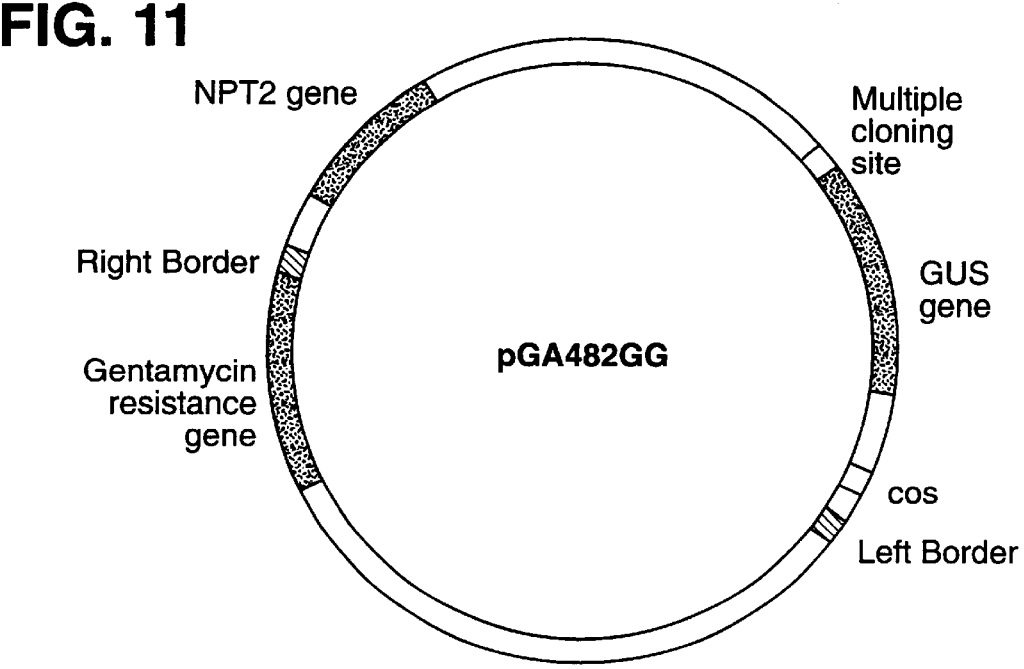
FIG. 11 depicts the structure of binary plasmid pGA482GG.

The isolation, DNA sequenc, modification, and expression of these genes in plant cells is described by Hu et al., *Arch. Virol.*, 130, 17 (1993). Briefly, after isolation and sequencing, the genes were engineered into the plant expression cassette, pUC18cpexpress, according to Slightom, *Gene*, 100, 251 (1991). Use of this methodology and expression cassette produced SQMV coat protein clones attached in frame to the cucumber mosaic virus 5' untranslated leader. The fusions are driven by the 35S promoter and use the 35S terminator (FIG. 4). The modified genes were then isolated after HindIII digestion and in a single step, introduced into the Upjohn binary plasmid pGA482GG (FIG. 11). This plasmid is a derivative of pGA482 (An, *Methods in Enzymol.*, 153, 292 (1987)). The two coat protein cassettes are oriented in the same direction as the NPTII gene. The genes are present as single copies.

5. Papaya Ringspot Virus

A plant expressible PRV gene was isolated via polymerase chain reaction using specific oligonucleotide primers. For further information refer to Applicants' Assignees copending patent application Ser. No. 08/366,881 entitled "Papaya Ringspot Virus Coat Protein Gene" filed on Dec. 30, 1994, now U.S. Pat. No. 5,498,974, incorporated by reference herein. After isolation and sequencing the gene was engineered into the plant expression cassette pUC 18cp express according to Slightom, ibid. (1991).

6. Multiple Coat Protein Constructions

Single coat protein expression cassettes were placed together in various combinations in order to obtain binary plasmids capable of transferring more than one plant-expressible gene into plant genomes.

(a) ZYMV72/WMBN-22

Figure 5:
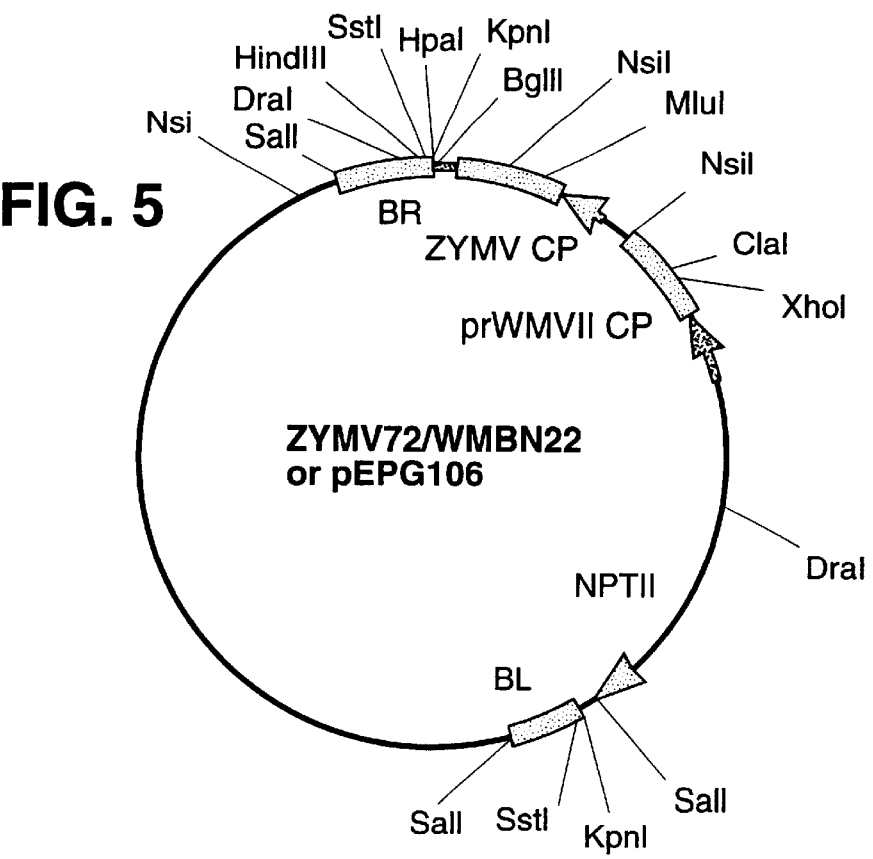
FIG. 5 depicts the structure of binary plasmid pEPG106.
Figure 6:
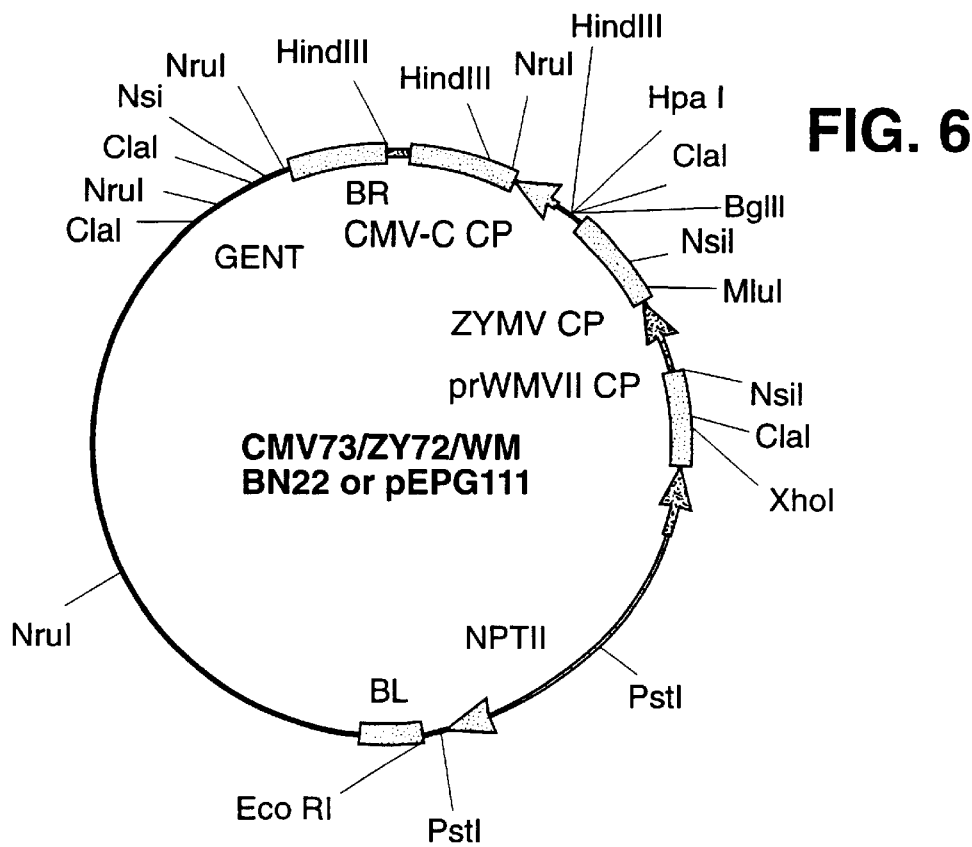
FIG. 6 depicts the structure of binary plasmid pEPG111.

ZYMV72/WMBN22 is derived from the binary plasmid pPRBN, into which expression cassettes for ZYMV and WMV2 coat proteins have been inserted. The expression cassettes were inserted sequentially into the unique BglII restriction site of pPRBN. To accomplish this, a site was introduced 5' to the 35S promoter, and a BglII site was introduced 3' to the poly A addition sequence of the WMV-2 and the ZYMV expression cassettes. BamHI and BglII sites were introduced by the use of appropriate oligonucleotide primers during PCR amplification of the cassettes. PCR products were digested with BamHI and BglII to produce the appropriate ends. The WMV-2 cassette carrying BamHI/BglII ends was inserted into the unique BamHI/BglII termini site to yield ZYMV72/WMBN22 (FIG. 5). The binary cassette is designated ZW.

(b) CMV73/ZYMV72/WMBN22

The CMV-c coat protein expression cassette was inserted into the unique HindIII site of ZYMV72/WMBN22 yielding CMV73/ZYMV72/WMBN22 (FIG. 5). This tertiary cassette is designated CZW.

(c) CMV-WL41/ZYMV72/WMBN22 (C-WLZW)

Figure 7:
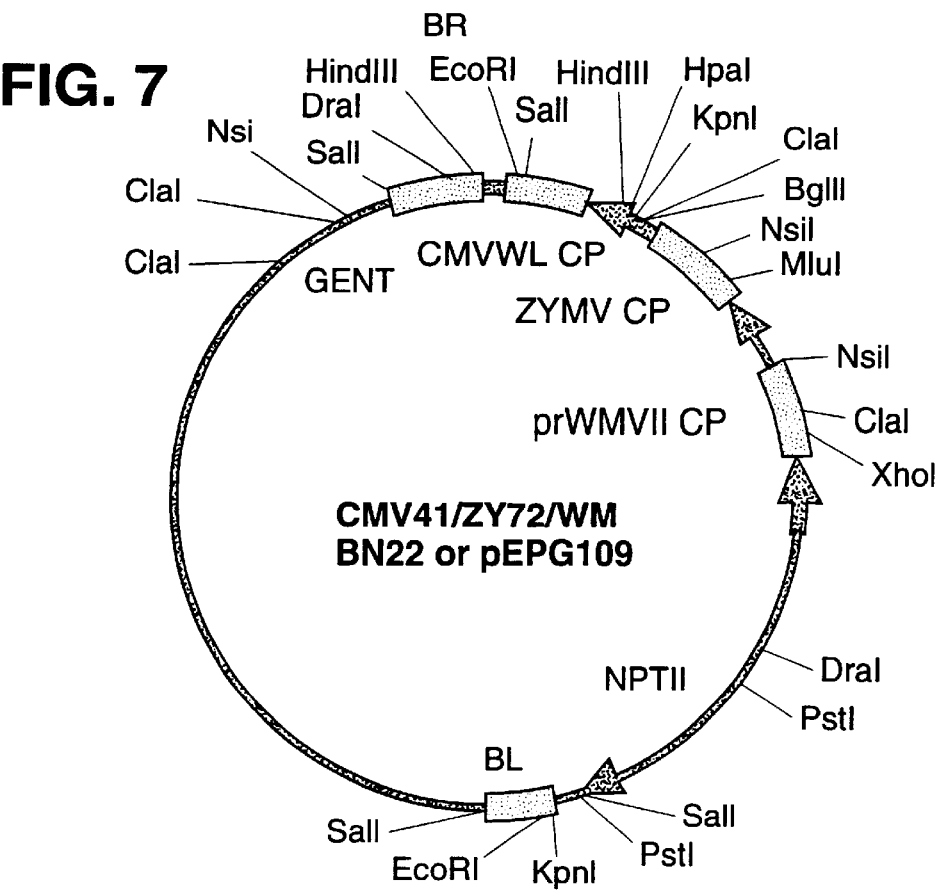
FIG. 7 depicts the structure of binary plasmid pEPG109.
Figure 8:
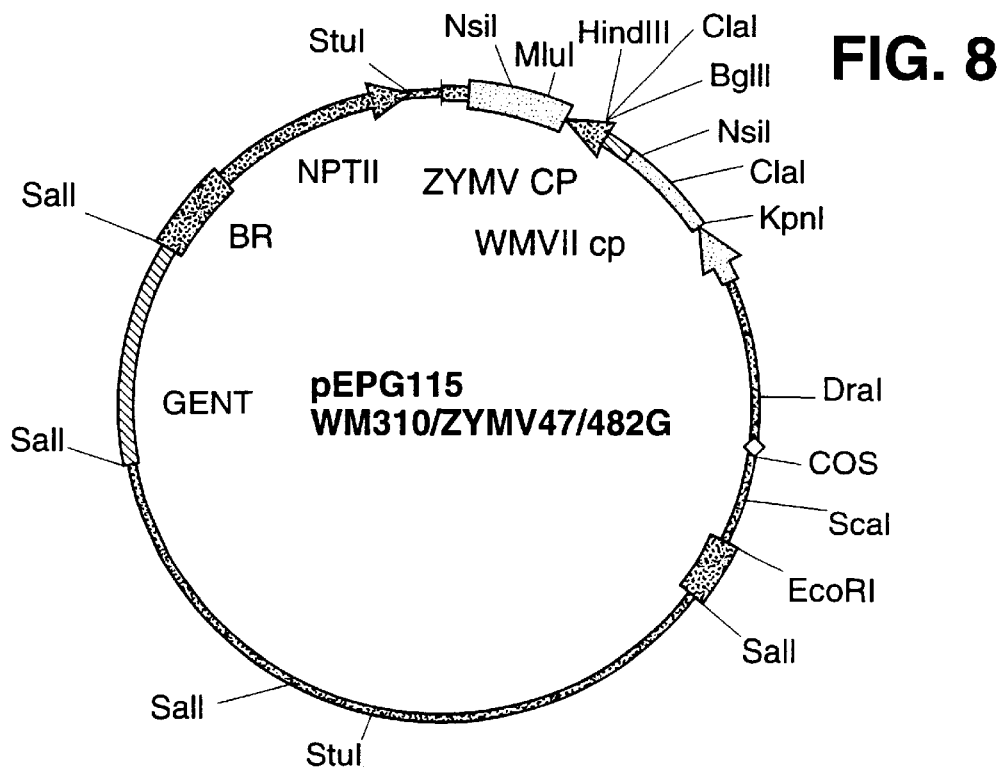
FIG. 8 depicts the structure of binary plasmid pEPG115.

Expression cassettes for CMV-white leaf (WL) strain, ZYMV, and WMV2 coat protein genes were inserted into the binary plasmid pPRBN to obtain CMV-WL41/ZYMV72/WMV2 (C-WLZW). To install this combination of virus coat protein cassettes in pPRBN, a CMV-white leaf strain coat protein gene expression cassette was inserted into ZYMV72/WMVN22 (see above for construction of ZYMV72/WMBN22). To construct the CMV-WL cp expression cassette, Namba et al., *Gene*, 107, 181 (1991) inserted the coat protein coding region of CMV-WL into cpexpress. A HindIII fragment containing the CMV-WL expression cassette was inserted into the HindIII site of ZYMV72/WMBN22 to obtain CMV-WL41/ZYMV72/WMBN22 (FIG. 7). This binary plasmid is designated C$_{WL}$ZW.

(d) WM310/ZYMV47/482G

A HindIII fragment harboring the ZYMV cp expression cassette described above was installed into the unique HindIII site of pGA482G to obtain ZYMV47/482G. Next, a BamHI fragment harboring the WMV2 cassette described above was inserted into the unique BglII site of ZYMV47/482G to obtain WMV310/482G. This construct is designated WZ.

(e) PRVcpwm16S/WZ$_{WL}$41/ZY72/WMBN22

Figure 9:
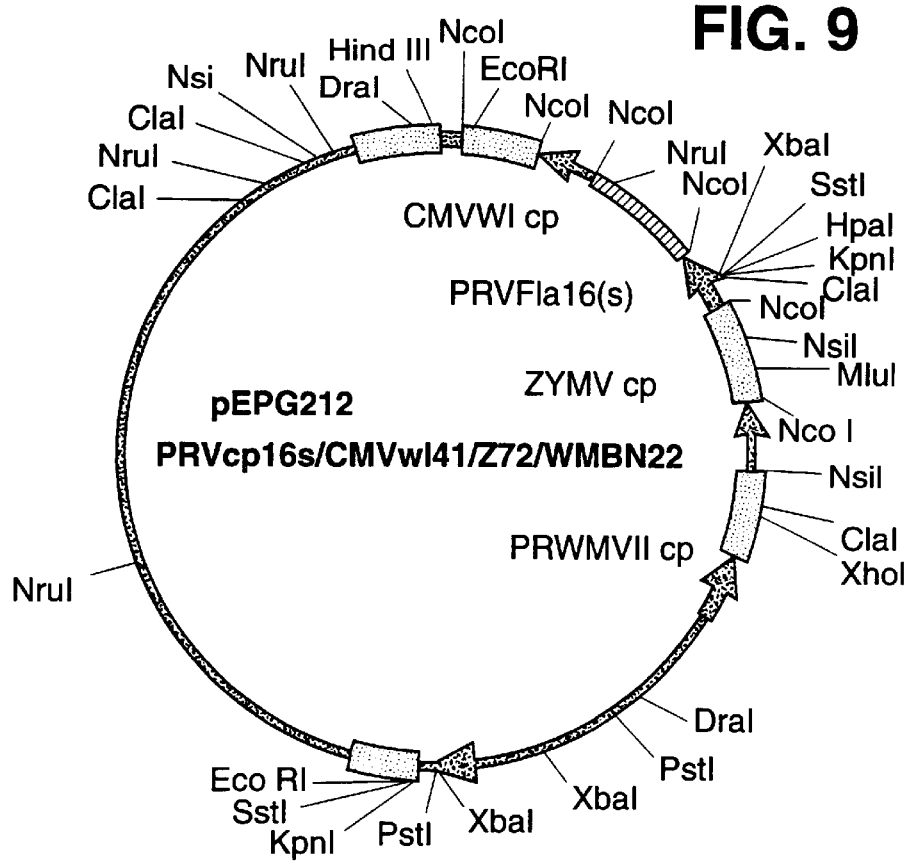
FIG. 9 depicts the structure of binary plasmid pEPG212.

Expression cassettes for PRV-FL strain (for further information refer to Applicants' Assignees co-pending patent application Ser. No. 08/366,881 entitled "Papaya Ringspot Virus Coat Protein Gene" filed on Dec. 30, 1994, now abandoned, and incorporated by reference herein), CMV-whiteleaf strain, ZYMV and WMV-2 coat protein genes were inserted into the binary plasmid pPRBN to obtain PRVcpwm16S/C$_{WL}$41/ZY72/WNBN22 (FIG. 9). This construct is designated PCZW.

(f) PNIa22/C$_{WL}$41/ZY72/WMBN22

Figure 10:
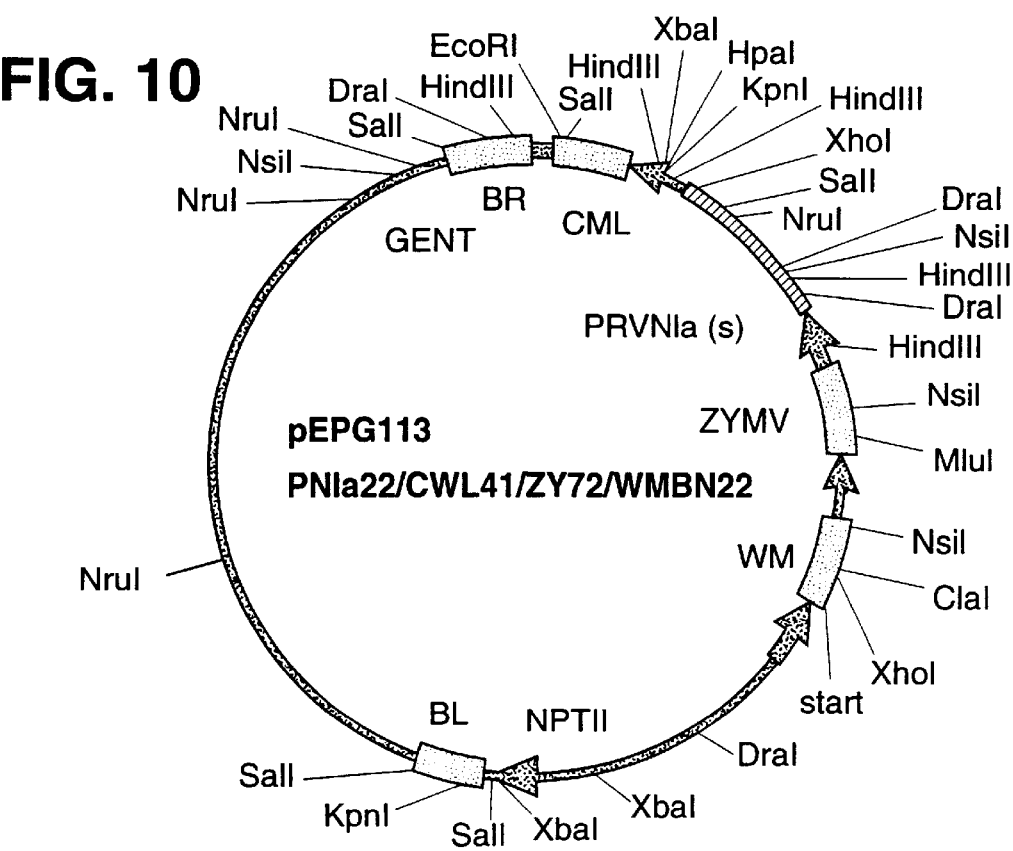
FIG. 10 depicts the structure of binary plasmid pEPG113.

Expression cassettes for the PRV-P strain PNIa gene (for further information refer to Applicants' Assignees copending patent application Ser. No. 08/366,490 entitled "Papaya Ringspot Virus Protease Gene" filed on Dec. 30, 1994, now U.S. Pat. No. 5,877,403 and incorporated by reference herein) and the coat protein gene cassettes for CMV-WL strain ZYMV and WMV-2 were inserted into the binary plasmid pPRBN to obtain PNIa22/C$_{WL}$41/ZY72WMBN22 (FIG. 10). This construct is designated PNIa CZW.

(g) SQ21/SQ42/WMBN22/ZY72/PRVcpwm16s/C$_{WL}$41

Figure 12:
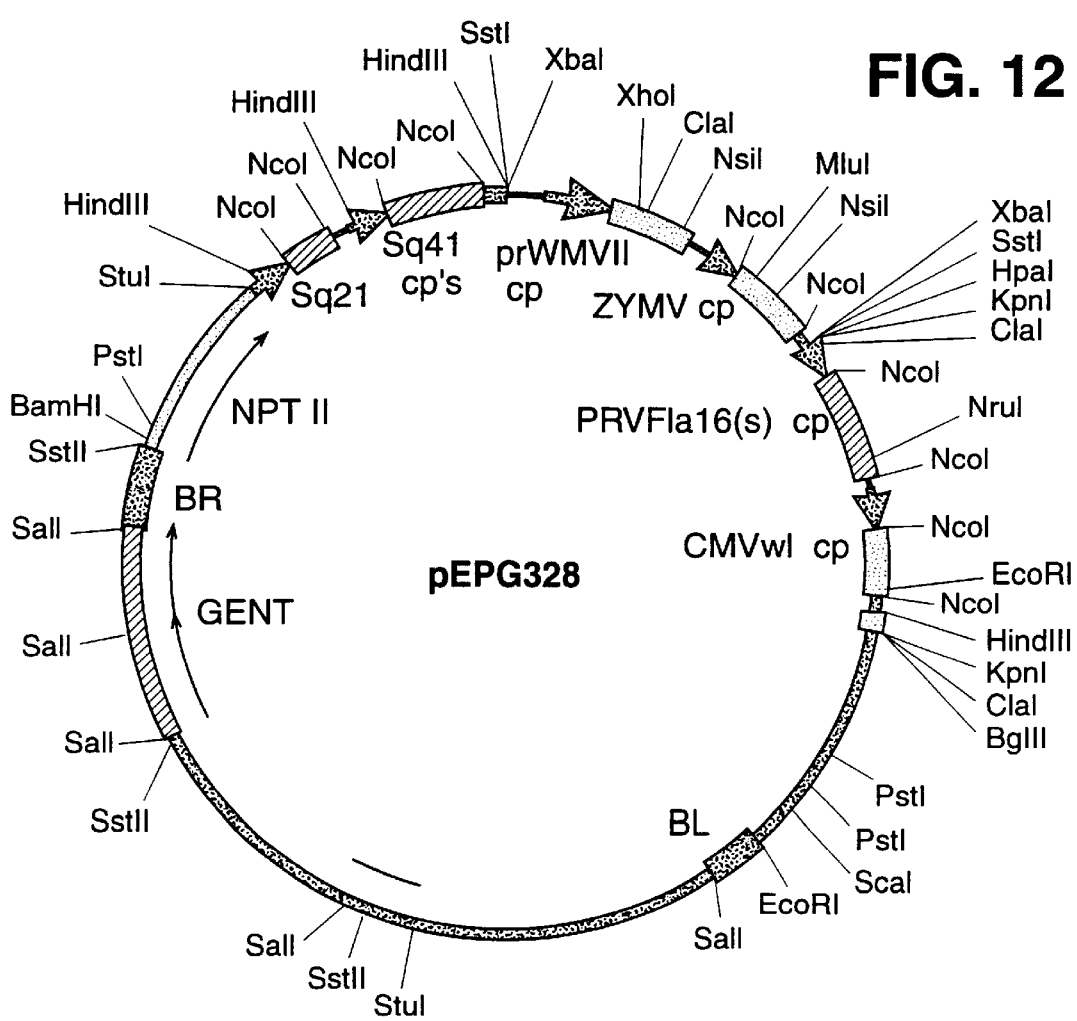
FIG. 12 depicts the structure of binary plasmid pEPG328.

Expression cassettes were made for the coat protein genes of the WMV-2, ZYMV, the PRV-FL and the CMV-WL strain and the two coat protein genes from SqMV and inserted into binary plasmid pGA482GG (FIG. 12). This construct is designated SWZPC.

C. Squash Transformation

After removal of seed coats, the seeds were surfaced sterilized for 20–25 minutes in a 20% solution of sodium hypochlorite (Clorox) containing tween 20 (200 ul/1000 mls.) Disinfestation was followed by three 100 ml rinses in sterile distilled water. Seeds were germinated in 150×25 mm culture tubes containing 20 mls of 1/4 strength Murashige and Skoog minimal organics (MS) medium solidified with 0.8% Difco Bacto Agar. After 5–7 days cotyledons were removed from the seedlings, and shoot tips were excised and transferred to GA7 vessels (Magenta Corp.) containing 75 mls MS medium solidified with 1.5% Difco Bacto Agar. Unless stated otherwise, all cultures were incubated in a growth room at 25° C. with a photoperiod of 16 hours of light. Light was provided with both cool fluorescent (Phillips F40CW) and plant growth (General Electric F40-PF) lamps.

Leaf pieces (0.5 cm) were collected from in vitro plants and soaked in *Agrobacterium tumefaciens* broth culture (OD 600 0.1–0.2) and transferred to 100×20 mm petri dishes containing 40 mls of MS medium supplemented with 1.2 mg/liter 2,4,5-trichlorophenoxyacetic acid (2,4,5-T) and 0.4 mg/liter benzylaminoacid (BAP) (MS-I) with 200 $\mu$M AS. Plates were incubated at 23° C. After two-three days leaf pieces were transferred onto MS-I medium containing 500 mg/liter carbenicillin, 200 mg/liter cefotaxime and 150 mg/liter kanamycin sulfate (MS-IA). After ten days, leaves were transferred to fresh MS-IA medium Thereafter, tissue was transferred to fresh MIS-IA medium every three weeks. After approximately 16–24 weeks kanamycin resistant embryogenic callus was harvested and transferred to roller tubes containing liquid MS minimal organics medium supplemented with 500 mg/liter carbencillen and 150 mg/liter kanamycin sulfate and 1.03 mg/l CACl$_2$2H$_2$O. Developing embryo were harvested and transferred to MS minimal organics medium containing 20 mg AgNO$_3$. Germinating embryos were subcultured to fresh medium until rooted shoots were obtained. Plantlets were transferred to soil for R$_1$ seed production.

D. Plant Analysis

Kanamycin resistant transformants were analyzed for the expression of the NPT II gene by ELISA using a commercially available ELISA kit (5-Prime 3-Prime, Boulder, Colo.). Polymerase chain reactions using the appropriate primers were conducted in order to amplify the NPT II gene (adjacent to the right border) and the coat protein gene closest to the left border. Some lines were further characterized using Southern Blot Analysis. Expression of the viral coat protein gene in putatively transformed plants was detected by ELISA utilizing alkaline phosphatase-conjugated antibodies according to the protocol of M. F. Clark et al., *J. Gen. Virol.,* 34, 475 (1977). Antisera to CMV-C, WMV-2-NY, and ZYMV-FL, were provided by D. Gonsalves (Cornell University, Geneva, N.Y.).

The presence or absence of the T-DNA in the R$_1$ and subsequent generations was determined by ELISA tests for the selectable NPT II marker gene. PCR or Southern analysis was used to follow the inheritance in line ZW20 whose advance generations lacked the NPT II gene.

D. Inoculation Procedure

Segregating R$_1$ or R$_2$ progeny along with the appropriate control lines were germinated in the greenhouse. Prior to viral inoculation, cotyledon samples were collected for NPT II ELISA assays. Carborundum dusted cotyledons were mechanically inoculated on six-day-old seedlings with a 1×10$^{-1}$ wt/vol dilution of CMV strain C, ZYMV strain FL, or WMV-2 strain NY (Available from D. Gonsalves, Cornell University), which were propagated in *Cucumis sativus, Cucurbita pepo* and *Phaseolus vulgaris* respectively. Plants were inoculated with virus in the greenhouse. Approximately 7–10 days post inoculation, plants were transplanted into the field. In some trials non-inoculated control plants were included in order to monitor some spread of the virus by aphids. Data on symptomatic development were gathered prior to review of the NPT II ELISA results, so the scoring was done without knowledge of the transgenic status of the individual segregant being evaluated.

Plants were given a disease severity rating of 0–9 based on foliage symptoms (0=non-symptomatic, 3=symptoms on inoculated leave and/or very mild symptoms on new growth, 5=moderate systemic spread 7=severe systemic spread, 9=severe systemic spread and stunting). Fruits were also scored according to symptom severity (0=non-symptomatic, 3=mild green blotching of fruit. 5=moderate discoloration. 7=severe discoloration, 9=fruit discoloration and distortion). Each line was then given a disease rating for fruit and foliage which was an average of the individual plant ratings.

E. Field Trial Plot Design

Field trials were carried out under permits issued by Animal and Plant Health Inspection Service (APHIS) of the United States Department of Agriculture (USDA). A design was employed in which each row consisting of a transgenic line was paired with a row containing its non-transgenic counterpart as a control. Each row consisted of 15 plants, two feet apart, with five feet between rows. Two to three replications of each transgenic line were incorporated in each test. Plots were surrounded by a minimum 30 foot border zone of non-transgenic squash plants in order to reduce the flow of transgenic pollen out of the trial site and to monitor for viral spread in the field. Transgenic material incorporated into the test included R$_1$ and R$_2$ progeny from self pollinated or backcrossed R$_o$ yellow crookneck inbred lines. In some cases, a transgenic inbred line was caused to the appropriate nontransgenic inbred line in order to produce the transgenic versions of the commercial squash hybrids, Pavor or Dixie.

F. Results

ZW Constructs

Line ZW20 was developed from an $R_o$ plant which was transformed with ZYMV72/WMBN22. Observations made during field trials 1 and 2 on the $R_1$ population revealed that all the plants containing the NPT II insert remained resistant to ZYMV and WMV-2 throughout the course of the trial.

Line ZW19 was also developed from an $R_o$ plant which was transformed with ZYMV72/WMVN22. In contrast to line ZW-20, ZW-19 provided a reduction in symptom development when inoculated with either ZYMV or WMV-2 (Table 1).

TABLE 1

Symptom development on transgenic inbred yellow crookneck squash (YC) squash lines 40 to 47 days post inoculation with a 1/10 wt/vol dilution of ZYMV-FL strain or WMV-2 NY strain conducted during our 1991 and 1992 trials.
(# (%) symptomatic plants)

| Line | NPT II | 1991 WMV-2 trial | | 1992 WMV-2 trial | | 1992 ZYMV trial | |
|---|---|---|---|---|---|---|---|
| ZW-19 | + | — | — | 14/14 | (100) | 11/11* | (100) |
|  | − | — | — | 16/16 | (100) | 19/19 | (100) |
| ZW-20 | + | 0/14 | (0) | 0/5 | (0) | — | — |
|  | − | 5/18 | (28) | 10/25 | (40) | — | — |

*mild

CW Constructs

Transgenic squash plants harboring expression vectors with CMV-C and WMV-2 CP genes were inoculated with either CMV strains V27, V33, or V34 (for further information, see Applicants' Assignees copending patent application Ser. No. 08/367,789 entitled "Plants Resistant to V27, V33, or V34 Strains of Cucumber Mosaic Virus" filed on Dec. 30, 1994, now abandoned incorporated by reference herein), which are capable of infecting transgenic plants expressing CMV-C coat protein. A majority of the transgenic plants were resistant to challenge with these heterologous CMV strains, unlike the transgenic lines harboring a CMV-C CP alone. The remaining plants that were infected had greatly reduced symptoms relative to transgenic plants with CMV-C CP alone.

CZW Constructs

Line CZW-3 was developed from an $R_o$ plant transformed with CMV73/ZYMV72/WMBN22. It remained asymptomatic in field trials to infection from CMV-C, ZYMV-FL or WMV-2, whether each inoculation applied individually or in a cocktail containing all three viral agents (Table 2).

Line CZW-40 was developed from an $R_o$ plant transformed with $C_{WL}$41./ZWMV-72/WMBN22. It failed to provide any protection against infection when inoculation with either CMV-C, ZYMV-FL or WMV-2 NY (Table 2).

TABLE 2

Symptom Development on Squash Plants after inoculation with a 1/10 w/vol dilution of CMV-C, ZYMV-FL or WMV-2-NY

| Line | NPT II | Challenge | Symptomatic Ratio | % | Disease Rating foliar | fruit |
|---|---|---|---|---|---|---|
| CZW-3 | + | CMV-C | 1/13 | 0.7 | 0.4 | 0.0 |
|  | − |  | 6/6 | 100 | 8.5 | — |

TABLE 2-continued

Symptom Development on Squash Plants after inoculation with a 1/10 w/vol dilution of CMV-C, ZYMV-FL or WMV-2-NY

| Line | NPT II | Challenge | Symptomatic Ratio | % | Disease Rating foliar | fruit |
|---|---|---|---|---|---|---|
| CZW-40* | + | CMV-C | 4/4 | 100 | 5.0 | — |
|  | − |  | 11/11 | 100 | 9.0 | — |
| CZW-3 | + | ZYMV-FL | 0/14 | 0 | 0.0 | 0.0 |
|  | − |  | 4/4 | 100 | 8.0 | 7.0 |
| CZW-40 | + | ZYMV-FL | 9/9 | 100 | 9.0 | — |
|  | − |  | 5/5 | 100 | 7.0 | — |
| CZW-3 | + | WMV-2-NY | 0/40 | 0 | 0.0 | 0.0 |
|  | − |  | 15/15 | 100 | 7.0 | 7.0 |
| CZW-40 | + | WMV-2-NY | 11/11 | 100 | 7.0 | — |
|  | − |  | 3/3 | 100 | 7.0 | — |

* Greenhouse screen

The fruit and foliage had disease ratings of 0. In contrast, 100% of the cp- segregants developed severe symptoms of virus infection on both their foliage and fruit. Disease ratings for CP- segregants ranged between 7.0 and 9.0 (Table 3). This trial demonstrated that by placing the coat protein genes in combination, one can obtain resistance against simultaneous infection by different viruses, in both inbred and hybrid lines.

TABLE 3

Field Trial 3 Results
Symptom development on squash plants 55 days after simultaneously inoculated with a 1/10 w/v mixture of CMV-C, ZYMV-FL and WMV-2 NY.

| Line | CP | Symptomatic ratio | % | Disease Rating foliage | fruit |
|---|---|---|---|---|---|
| Dixie CZW-3 | + | 0/27 | 0 | 0.0 | 0.0 |
|  | − | 30/30 | 100 | 8.4 | 7.0 |
| Pavo CZW-3 | + | 0/27 | 0 | 0.0 | 0.0 |
|  | − | 33/33 | 100 | 7.0 |  |
| YS20CZW-3 | + | 0/40 | 0 | 0.0 | 0.0 |
|  | − | 15/15 | 100 | 7.0 | 7.0 |
| Dixie | + | — | — | — | — |
|  | − | 14/14 | 100 | 8.7 | 7.0 |
| Pavo | + | — | — | — | — |
|  | − | 24/24 | 100 | 8.9 | 7.0 |

For the third testing season an $R_2$ generation of CZW-3 was produced by selfing a CP positive $R_1$ CZW-3 segregant. Two transgenic hybrid lines, equivalent to Asgrow's commercial hybrids Pavo and Dixie were also produced using this transgenic inbred line as one of the parents. The progeny of the selfed inbred line exhibited the expected segregation ratio (based on NPT II ELISA) of 3:1 for the inserted gene, whereas both of the hybrid lines exhibited the expected 1:1 ratio. The transgenic inbred and hybrid progeny were inoculated with an inoculum mixture containing a 1/10 w/v dilution of all three virus, CMV-C, WMV-2-NY and ZYMV-FL. Table 3 shows that segregants were completely resistant to infection by all three viruses.

The results presented here confirm that coat protein genes provide multi-viral resistance when inserted in combination. For example transgenic line CZW-3 remained asymptomatic in all three virus trials (CMV, ZYMV, and WMV-2) in which they were inoculated with each virus singly, as well as remaining asymptomatic when inoculated with all three viruses simultaneously. The ability to obtain lines with resistance to multiple virus infection is essential for the development of commercially useful squash cultivars, since under commercial field conditions it is common to find infection by more than one virus during a growing season.

In these trials, it was also observed that when multiple coat protein genes are inserted in a single construct, all the genes in the construct provide similar levels of efficacy. Line CZW-3 which provides a high level of resistance to CMV-C also provides a high level resistance to ZYMV-FL and WMV-2-NY. In construct transgenic lines such as ZW-19, which displayed only moderate resistance (i.e., milder symptom resistance development) for WMV-2 also exhibited only moderate resistance to ZYMV. Furthermore greenhouse screens on transgenic line CZW40 demonstrated that this line, which failed to provide resistance to CMV-C, also failed to provide resistance to ZYMV-FL and WMV-2-NY. This coordinated level of action between genes in a multiple gene construct may reflect the effect of the location within the plant genome into which the genes insert. In any event, this phenomenon provides a method to greatly enhance the probability of finding individual transgenic lines with high levels of resistance against multiple viral agents.

EXAMPLE II

Introduction of Multi-Cp Gene Cassettes into Cantaloupe

1. Cantaloupe Transformation

Cantaloupe inbred lines were transformed with the multiple gene constructs listed above using a modification of the procedure of Fang and Grumet *Molec. Plant Microbe Interactions*, 6, 358 (1993). Rooted transformed plants were transferred to the greenhouse and $R_1$ produced.

Plant Analysis/Inoculation Procedure

Transgenic plants were analyzed and inoculated as described in Example I listed above.

2. Results

ZW constructs. Line CA76-ZW-102-29 provided resistance to infection by both ZYMV-FL or WMV-2-NY. In contrast all other lines failed to provide resistance against infection by either ZYMV or WMV-2 (Table 4).

TABLE 4

Symptom Development on Transgenic Cantaloupe Plants after inoculation with a 1/10 w/vol dilution of ZYMV-FL or WMV-2-NY

| Line | NPT II | Challenge | Symptomatic Ratio | % | Disease Rating |
|---|---|---|---|---|---|
| CA-ZW-102-29 | + | ZYMV-FL | 0/30 | 0 | 0.0 |
|  | − |  |  |  |  |
|  | + | WMV-2-NY | 0/9 | 0 | 0.0 |
|  | − |  | 2/2 | 100 | 5.0 |
| CA-ZW-115-38 | + | ZYMV-FL | 0/30 | 0 | 0.0 |
|  | − |  |  |  |  |
|  | + | WMV-2-NY | 9/17 | 0 | 0.0 |
|  | − |  | 6/8 | 75 | 4.0 |

PCZW construct. Line CA95 PXZW-1 provided resistance to infection by CMV-C, ZYMV-FL and WMV-2. The line has traditional resistance to PRV so that the efficacy of the PRV insert could not be ascertained. In contrast numerous PCZW transgenic lines failed to provide resistance against CMV-C or ZYMV-FL. Inoculation of these lines with WMV-2-NY are still in progress (Table 5).

TABLE 5

Symptom Development on Transgenic Cantaloupe lines after inoculation with a 1/10 w/vol dilution of ZYMV-FL, WMV-2-NY, or CMV-C

| Line | NPT II | Challenge | Symptomatic Ratio | % | Disease Rating |
|---|---|---|---|---|---|
| CA95-PCZW-93351-1 | + | CMV-C | 1/12 | (08) | 0.6 |
|  | − |  | 3/3 | (100) | 6.3 |
|  | + | WMV-2-NY | 1/9 | (11) | 0.5 |
|  | − |  | 2/2 | (100) | 5.0 |
|  | + | ZYMV-FL | 6/8 | (75) | 4.2 |
|  | − |  | 6/6 | (100) | 9.0 |
| CZ95-PCZW-93356-1 | + | CMV-C | 9/9 | (100) | 7.0 |
|  | − |  | 4/4 | (100) | 7.0 |
|  | + | ZYMV | 10/10 | (100) | 7.0 |
|  | − |  | 5/5 | (100) | 7.0 |
| CA95-PCZW-93356-6 | + | CMV-C | 9/9 | (100) | 7.0 |
|  | − |  | 1/1 | (100) | 9.0 |
|  | + | ZYMV | 10/10 | (100) | 7.0 |
|  | − |  | 1/1 | (100) | 7.0 |

SWZPC Construct. Although these lines have not yet been evaluated for resistance PCR analysis has verified that 27/36 (75%) of the cantaloupe lines produced with this construct contained all six cp genes plus the NPT II selectable marker gene. This demonstrated that Agrobacterium mediated transformation can be used to transfer at least seven (but probably many more) linked genes in a binary plasmid to plant cells with subsequent recovery of intact plants containing all seven linked gene inserts.

EXAMPLE III

Introduction of Multi-Cp Gene Cassettes into Cucumber

1. Cucumber Transformation

Cucumber inbreds were transformed with the multiple coat protein gene constructs listed above, using a modification of the procedure of Sarmento et al., *Plant Cell Tissue and Organ Culture*, 31, 185 (1992). Rooted plants were transferred to the greenhouse and $R_1$ seed produced. Transgenic plants were analyzed and inoculated as described in Example I above.

2. Results

CZW Constructs. Line GA715 CZW 7, 95, 33, 99 were resistant to both ZYMV-FL and WMV-2-NY (these lines have been traditionally bred for resistance to CMV-C, so the efficacy of the CMV coat protein insert could not be ascertained) (Table 6).

TABLE 6

Symptom Development on Transgenic Cucumber Lines after inoculation with a 1/10 w/vol dilution of ZYMV-FL, ZYMV-CA, or WMV-2-NY

| Line | NPT II | Challenge | Symptomatic Ratio | % | Disease Rating |
|---|---|---|---|---|---|
| GA715 CZW-7 | + | ZYMV-FL | 0/8 | 0 | 0.0 |
|  | − |  | 7/7 | 100 | 6.4 |
|  | + | WMV-2-NY | 0/5 | 0 | 0.0 |
|  | − |  | 8/9 | 89 | 4.4 |
| CA715-CZW-33 | + | ZYMV-FL | 0/6 | 0 | 0.0 |
|  | − |  | 9/9 | 100 | 6.9 |
|  | + | WMV-2-NY | 0/6 | 0 | 0.0 |
|  | − |  | 8/8 | 100 | 4.3 |

TABLE 6-continued

Symptom Development on Transgenic Cucumber Lines after inoculation with a 1/10 w/vol dilution of ZYMV-FL, ZYMV-CA, or WMV-2-NY

| Line | NPT II | Challenge | Symptomatic Ratio | % | Disease Rating |
|---|---|---|---|---|---|
| GA715-CZW-95 | + | ZYMV-FL | 0/11 | 0 | 0.0 |
| | − | | 2/2 | 100 | 5.0 |
| | + | WMV-2-NY | 0/10 | 0 | 0.0 |
| | − | | 2/2 | 100 | 5.0 |
| GA715-CZW-99 | + | ZYMV-F | 0/8 | 0 | 0.0 |
| | − | | 6/6 | 100 | 6.7 |
| | + | WMV-2-NY | 0/7 | 0 | 0.0 |
| | − | | 5/5 | 100 | 3.0 |

PNIa CZW Construct. Line GA715 PNIa CZW - 21 was resistant to CMV-C, ZYMV-FL and PRV-P-HA while line GA715 PNIaCZW-15 was susceptible to ZYMV-FL and WMV-2-NY (Table 7).

TABLE 7

Symptom Development on Transgenic Cucumber lines after inoculation with a 1/10 w/vol dilution of ZYMV-FL, WMV-2-NY, or PRV-P-HA.

| Line | NPT II | Challenge | Symptomatic Ratio | % | Disease Rating |
|---|---|---|---|---|---|
| GA715 PNIaCZW-21 | + | ZYMV-FL | 0/7 | 0 | 0.0 |
| | − | | 2/2 | 100 | 7.0 |
| | + | CMV- | 0/4 | 0 | 0.0 |
| | − | Carna-5 | 4/11 | 44 | 2.2 |
| | + | WMV-2-NY | NT | NT | NT |
| | − | | NT | NT | NT |
| | + | PRV-P-HA | 0/3 | 0 | 0.0 |
| | − | | 6/6 | 100 | 3.0 |
| GA715 PNIaCZW-15 | + | ZYMV-FL | 2/2 | 100 | 3.0 |
| | − | | 12/12 | 100 | 5.0 |
| | + | WMV-2-NY | 4/4 | 100 | 3.0 |
| | − | | 10/10 | 100 | 3.0 |
| | + | PRV-P-HA | NT | NT | NT |
| | − | | NT | NT | MT |
| | + | CMV-C | NT | NT | NT |
| | − | Carna-5 | NT | NT | NT |

EXAMPLE IV

Introduction of Multi CP Gene Cassette into Watermelon

1. Watermelon Transformation

Watermelon inbreds were transformed with multiple coat protein gene cassettes, WZ listed above, using a modification of the procedure described by Choi et al., *Plant Cell Reports*, 344 (1994).

2. Plant Analysis/Inoculation Procedure

Transgenic plants were analyzed and inoculated as described in Example I above.

3. Results

WZ construct. Lines WA$_3$WZ-20-14 was resistant to ZYMV-FL and WMV-2-NY (Table 8).

TABLE 8

Symptom Development on Transgenic Watermelon lines after inoculation with a 1/10 w/vol dilution of ZYMV-FL or WMV-2-NY

| Line | NPT II | Challenge | Symptomatic Ratio | % | Disease Rating |
|---|---|---|---|---|---|
| WA$_3$WZ-20-14 | + | ZYMV-FL | 0/14 | 0 | 0.0 |
| | − | | 11/11 | 100 | 9.0 |
| | + | WMV-2-NY | 0/13 | 0 | 0.0 |
| | − | | 1/10 | 100 | 9.0 |

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A chimeric recombinant DNA molecule comprising:

at least three tandemly linked DNA sequences, wherein each DNA sequence comprises a promoter operably linked to a DNA sequence which encodes a viral coat protein, wherein said tandemly linked DNA sequences impart substantially the same level of resistance against viral disease to plant cells caused by each of the viruses from which the tandemly linked DNA sequences originated, and further wherein said viruses are chosen from the group consisting of potyviruses, cucomoviruses, and comoviruses.

2. The DNA molecule of claim 1 wherein said DNA sequences further comprise a selectable marker gene, a reporter gene or a combination thereof that enables identification of plant cells transformed with said DNA molecule.

3. The DNA molecule of claim 2, wherein the DNA sequences are flanked by two selectable marker genes, two reporter genes or a combination thereof.

4. The DNA molecule of claim 1 wherein said viral coat proteins comprise the coat proteins of watermelon mosaic virus II, cucumber mosaic virus, and zucchini yellow mosaic virus.

5. The DNA molecule of claim 1 wherein the plant cells are cells derived from a member of the Cucurbitaceae family.

6. A method of imparting multi-virus resistance to a plant which is susceptible to viruses, comprising:

(a) transforming cells of said susceptible plant with a recombinant DNA molecule comprising at least three tandemly linked DNA sequences, each comprising a promoter functional in cells of said plant and operably linked to a DNA sequence encoding a coat protein of a virus which is capable of infecting said plant, wherein said viruses are chosen from the group of viruses consisting of potyviruses, cucomoviruses, and comoviruses;

(b) regenerating said plant cells to provide a differentiated plant; and (c) identifying a transformed plant which contains the tandemly linked DNA sequences which renders substantially equal levels of resistance against viral disease caused by said viruses to the plant.

7. The method of claim 6, wherein the expression of at least one of said DNA sequences imparts resistance to more than one virus.

8. The method of claim 6, wherein the plant is a dicot.

9. The method of claim 6, wherein the DNA molecule is part of a binary Ti plasmid and the plant cells are transformed by *A. tumefaciens* mediated transformation.

10. The method of claim 6, wherein the DNA sequences further comprise a selectable marker gene or a reporter gene that enables identification of said transformed plant.

11. The method of claim 6, wherein said DNA sequences further comprise the coat protein genes of watermelon mosaic virus II, cucumber mosaic virus and zucchini yellow mosaic virus.

12. The method of claim 6, wherein the susceptible plant is a member of the Cucurbitaceae family.

13. A transformed plant prepared by the method of claim 6.

14. A transformed plant cell prepared by the method of claim 6.

15. A transformed seed of the transformed plant of claim 13.

16. A hybrid plant, prepared by crossing the plant of claim 13, with a second plant, which is resistant to viral disease caused by said viruses.

* * * * *